United States Patent
Joly-Tonetti et al.

(10) Patent No.: US 12,174,172 B2
(45) Date of Patent: *Dec. 24, 2024

(54) METHOD FOR EVALUATING THE EFFICACY OF A COMPOSITION IN REDUCING THE EFFECTS OF CANCER THERAPEUTICS ON SKIN

(71) Applicant: Johnson & Johnson Consumer Inc., Skillman, NJ (US)

(72) Inventors: Nicolas Joly-Tonetti, Suisse (CH); Thomas Ondet, Val de Reuil (FR); Mario Monshouwer, Beerse (BE); Georgios N. Stamatas, Val de Reuil (FR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 435 days.

This patent is subject to a terminal disclaimer.

(21) Appl. No.: 17/083,915

(22) Filed: Oct. 29, 2020

(65) Prior Publication Data

US 2021/0190761 A1 Jun. 24, 2021

Related U.S. Application Data

(60) Provisional application No. 62/950,624, filed on Dec. 19, 2019.

(51) Int. Cl.
*G01N 33/50* (2006.01)
*C12N 5/071* (2010.01)

(52) U.S. Cl.
CPC ..... *G01N 33/5014* (2013.01); *G01N 33/5044* (2013.01); *C12N 5/0629* (2013.01); *C12N 2503/02* (2013.01); *C12N 2513/00* (2013.01)

(58) Field of Classification Search
CPC .......... G01N 33/5014; G01N 33/5044; C12N 5/0629; C12N 2503/02; C12N 2513/00
See application file for complete search history.

(56) References Cited

U.S. PATENT DOCUMENTS

| | | | |
|---|---|---|---|
| 10,092,495 B2 | 10/2018 | Msika et al. | |
| 10,175,230 B2 | 1/2019 | Msika et al. | |
| 2014/0275073 A1 | 9/2014 | Chang et al. | |
| 2019/0242880 A1 | 8/2019 | Bredif et al. | |
| 2022/0057383 A1* | 2/2022 | Ondet | G01N 33/5014 |

FOREIGN PATENT DOCUMENTS

| | | |
|---|---|---|
| CA | 2719442 A1 | 8/2011 |
| CN | 101155579 A | 4/2008 |
| RU | 2244005 C2 | 1/2005 |

OTHER PUBLICATIONS

Commandeur et al: Cancer Science: Epidermal growth factor receptor activation and inhibition in 3D in vitro models of normal skin and human cutaneous squamous cell carcinoma. vol. 103, No. 12, pp. 2120-2126 (Year: 2012).*

Lacouture et al: Support Care Cancer-Clinical practice guidelines for the prevention and treatment of EGFR inhibitor-associated dermatologic toxicities. vol. 19, p. 1079-1095 (Year: 2011).*

Mieremet et al [PLOS One: Epidermal barrier of skin models with chitosan modulated dermal matrix-Improved epidermal barrier formation in human skin models by chitosan modulated dermal matrices vol. 12, Issue. 3, p. 1-20 (Year: 2017).*

MatTek [https://www.mattek.com/products/epiderm] Web archived: Apr. 28, 2019 https://web.archive.org/web/20190428164659/https://www.mattek.com/products/epiderm/ (Year: 2019).*

Rais R, Zhao M, He P, Xu L, Deeken JF, Rudek MA. Quantitation of unbound sunitinib and its metabolite N-desethyl sunitinib (SU12662) in human plasma by equilibrium dialysis and liquid chromatography—tandem mass spectrometry (LC/MS/MS): application to a pharmacokinetic study. Biomed Chromatogr. 2012;26:230-3.

Herbst RS, Johnson DH, Mininberg E, Carbone DP, Henderson T, Kim ES, et al. Phase I/II trial evaluating the anti-vascular endothelial growth factor monoclonal antibody bevacizumab in combination with the HER-1/epidermal growth factor receptor tyrosine kinase inhibitor erlotinib for patients with recurrent non-small-cell lung cancer. J Clin Oncol. 2005;23:2544-55.

Wind S, Schmid M, Erhardt J, Goeldner RG, Stopfer P. Pharmacokinetics of afatinib, a selective irreversible ErbB family blocker, in patients with advanced solid tumours. Clin Pharmacokinet. 2013;52:1101-9.

Burris HA, Hurwitz HI, Dees EC, Dowlati A, Blackwell KL, O'Neil B, et al. Phase I safety, pharmacokinetics, and clinical activity study of lapatinib (GW572016), a reversible dual inhibitor of epidermal growth factor receptor tyrosine kinases, in heavily pretreated patients with metastatic carcinomas. J Clin Oncol. 2005;23:5305-13. doi:10.1200/JCO.2005.16.584.

Peus D, Hamacher L, Pittelkow MR. EGF-receptor tyrosine kinase inhibition induces keratinocyte growth arrest and terminal differentiation. J Invest Dermatol. 1997;109:751-6.

Tischer B, Huber R, Kraemer M, Lacouture ME. Dermatologic events from EGFR inhibitors: the issue of the missing patient voice. Support Care Cancer. 2017;25:651-60. doi:10.1007/s00520-016-3419-4.

Kwak EL, Shapiro GI, Cohen SM, Becerra CR, Lenz H-J, Cheng W-F, et al. Phase 2 trial of afatinib, an ErbB family blocker, in solid tumors genetically screened for target activation. Cancer. 2013;119:3043-51. doi:10.1002/cncr.28120.

Hanahan D, Weinberg RA. Hallmarks of cancer: the next generation. Cell. 2011;144:646-74. doi:10.1016/j.cell.2011.02.013.

(Continued)

*Primary Examiner* — Christian L Fronda
(74) *Attorney, Agent, or Firm* — Samuel J. Gee

(57) ABSTRACT

An epidermal tridimensional model exhibiting differentiating keratinocytes in a reconstituted stratum corneum model is disclosed. The model, which contains a cancer therapeutic at an amount effective to simulate chronic drug exposure, can be used to evaluate the potential of cancer therapeutics to produce skin related side effects. The method can also be used to evaluate the efficacy of a composition in reducing the effects of cancer therapeutics on skin.

7 Claims, 7 Drawing Sheets

(56) References Cited

OTHER PUBLICATIONS

Lacouture ME. Mechanisms of cutaneous toxicities to EGFR inhibitors. Nat Rev Cancer. 2006;6:803-12.
Takeda M, Nakagawa K. First-and second-generation EGFR-TKIs are all replaced to osimertinib in chemo-naive EGFR mutation-positive non-small cell lung cancer. International Journal of Molecular Sciences. 2019;20:146. doi:10.3390/ijms20010146.
Goss G, Tsai C-M, Shepherd FA, Bazhenova L, Lee JS, Chang G-C, et al. Osimertinib for pretreated EGFR Thr790Met-positive advanced non-small-cell lung cancer (AURA2): a multicentre, open-label, single-arm, phase 2 study. Lancet Oncol. 2016;17:1643-52. doi:10.1016/S1470-2045(16)30508-3.
Kari C, Chan TO, Rocha de Quadros M, Rodeck U. Targeting the epidermal growth factor receptor in cancer: Apoptosis takes center stage. Cancer Res. 2003;63:1-5.
Mascia F, Mariani V, Girolomoni G, Pastore S. Blockade of the EGF Receptor Induces a Deranged Chemokine Expression in Keratinocytes Leading to Enhanced Skin Inflammation. 2003.
Cubero DIG, Abdalla BMZ, Schoueri J, Lopes FI, Turke KC, Guzman J, et al. Cutaneous side effects of molecularly targeted therapies for the treatment of solid tumors. Drugs Context. 2018;7:1-11.
Yerushalmi R, Woods R, Ravdin PM, Hayes MM, Gelmon KA. Ki67 in breast cancer: prognostic and predictive potential. Lancet Oncol. 2010;11:174-83. doi:10.1016/S1470-2045(09)70262-1.
Sandilands A, Sutherland C, Irvine AD, McLean WHI. Filaggrin in the frontline: role in skin barrier function and disease. J Cell Sci. 2009;122 Pt 9:1285-94. doi: 10.1242/jcs.033969.
Getsios S, Amargo E V., Dusek RL, Ishii K, Sheu L, Godsel LM, et al. Coordinated expression of desmoglein 1 and desmocollin 1 regulates intercellular adhesion. Differentiation. 2004;72:419-33. doi:10.1111/j.1432-0436.2004.07208008.x.
Steinert PM, Marekov LN. Direct evidence that involucrin is a major early isopeptide cross-linked component of the keratinocyte cornified cell envelope. J Biol Chem. 1997;272:2021-30. doi:10.1074/jbc.272.3.2021.
Paul T, Schumann C, Rüdiger S, Boeck S, Heinemann V, Kächele V, et al. Cytokine regulation by epidermal growth factor receptor inhibitors and epidermal growth factor receptor inhibitor associated skin toxicity in cancer patients. Eur J Cancer. 2014;50:1855-63.
Danilenko DM, Phillips GDL, Diaz D. In Vitro Skin Models and Their Predictability in Defining Normal and Disease Biology, Pharmacology, and Toxicity. Toxicol Pathol. 2016;44:555-63. doi:10.1177/0192623316632074.
Klaeger S, Heinzlmeir S, Wilhelm M, Polzer H, Vick B, Koenig P-A, et al. The target landscape of clinical kinase drugs. Science. 2017;358. doi:10.1126/science.aan4368.
Rosell R, Carcereny E, Gervais R, Vergnenegre A, Massuti B, Felip E, et al. Erlotinib versus standard chemotherapy as first-line treatment for European patients with advanced EGFR mutation-positive non-small-cell lung cancer (EURTAC): A multicentre, open-label, randomised phase 3 trial. Lancet Oncol. 2012;13:239-46. doi:10.1016/S1470-2045(11)70393-X.
Yang Y, Zhang Y, Cao Z, Ji H, Yang X, Iwamoto H, et al. Anti-VEGF- and anti-VEGF receptor-induced vascular alteration in mouse healthy tissues. Proc Natl Acad Sci U S A. 2013;110:12018-23. doi:10.1073/pnas.1301331110.
Cross DAEE, Ashton SE, Ghiorghiu S, Eberlein C, Nebhan CA, Spitzler PJ, et al. AZD9291, an irreversible EGFR TKI, overcomes T790M-mediated resistance to EGFR inhibitors in lung cancer. Cancer Discov. 2014;4:1046-61. doi:10.1158/2159-8290.CD-14-0337.
Chu C, Choi J, Eaby-Sandy B, Langer CJ, Lacouture ME. Osimertinib: A Novel Dermatologic Adverse Event Profile in Patients with Lung Cancer. Oncologist. 2018;23:891-9.
Li J, Brahmer J, Messersmith W, Hidalgo M, Baker SD. Binding of gefitinib, an inhibitor of epidermal growth factor receptor-tyrosine kinase, to plasma proteins and blood cells: In vitro and in cancer patients. Invest New Drugs. 2006;24:291-7.
Swaisland HC, Smith RP, Laight A, Kerr DJ, Ranson M, Wilder-Smith CH, et al. Single-dose clinical pharmacokinetic studies of gefitinib. Clin Pharmacokinet. 2005;44:1165-77.
Togashi Y, Masago K, Fukudo M, Terada T, Ikemi Y, Kim YH, et al. Pharmacokinetics of erlotinib and its active metabolite OSI-420 in patients with non-small cell lung cancer and chronic renal failure who are undergoing hemodialysis. J Thorac Oncol. 2010;5:601-5. oi:10.1097/JTO.0b013e3181d32287.
Wind S, Schnell D, Ebner T, Freiwald M, Stopfer P. Clinical Pharmacokinetics and Pharmacodynamics of Afatinib. Clin Pharmacokinet. 2017;56:235-50. doi:10.1007/s40262-016-0440-1.
EMEA. European Medicines Agency: EMEA/H/C/002280—Annual report of the European Medicines Agency 2013. 2013;44 July. http://www.ema.europa.eu/docs/en_GB/document_library/EPAR_-_Public_assessment_report/human/002280/WC500152394.pdf.
Hudachek SF, Gustafson DL. Physiologically based pharmacokinetic model of lapatinib developed in mice and scaled to humans. J Pharmacokinet Pharmacodyn. 2013;40:157-76. doi:10.1007/s10928-012-9295-8.
Giri N, Masters JC, Plotka A, Liang Y, Boutros T, Pardo P, et al. Investigation of the impact of hepatic impairment on the pharmacokinetics of dacomitinib. Invest New Drugs. 2015;33:931-41.
Reddy VP, Walker M, Sharma P, Ballard P, Vishwanathan K. Development, verification, and prediction of osimertinib drug-drug interactions using PBPK modeling approach to inform drug label. CPT Pharmacometrics Syst Pharmacol. 2018;7:321-30.
Fabian MA, Biggs WH, Treiber DK, Atteridge CE, Azimioara MD, Benedetti MG, et al. A small molecule-kinase interaction map for clinical kinase inhibitors. Nat Biotechnol. 2005;23:329-36. doi:10.1038/nbt1068.
Villarroel MC, Pratz KW, Xu L, Wright JJ, Smith BD, Rudekl MA. Plasma protein binding of sorafenib, a multi kinase inhibitor: in vitro and in cancer patients. Invest New Drugs. 2012;30:1-15.
Davis MI, Hunt JP, Herrgard S, Ciceri P, Wodicka LM, Pallares G, et al. Comprehensive analysis of kinase inhibitor selectivity. Nat Biotechnol. 2011;29:1046-51. doi:10.1038/nbt.1990.
International Search Report; PCT/IB2020/060220; Dated Jan. 19, 2021.
H Vorsmann, et al.: Development of a human three-dimensional organotypic skin-melanoma spheroid model for in vitro drug testing.; Cell Death and Disease, vol. 4, No. 7, Jul. 1, 2013, p. e719.
Joly-Tonetti, et al.; 202 Cutaneous adverse drug reactions of oncology treatments; Journal of Investigative Dermatology, Elsevier, NL, vol. 139, No. 9, Sep. 1, 2019, pp. s249-s249.
Sarah Kuchler, et al.; Reconstructed skin models as emerging tools for drug absorption studies; Expert Opinion on Drug Metablolism & Toxicology, vol. 9, No. 10, Jul. 5, 2013, pp. 1255-1263.
Liang Chen, et al.; Skin Toxicity Assessment of Silver Nanoparticles in a 3D Epidermal Model Compared to 2D Keratinocytes; International Journal of Nanomedicine, vol. 14, Dec. 1, 2019, pp. 9707-9719.
Carla A. Brohem, et al.; Artificial skin in perspective: concepts and applications; Artificial skin; Pigment Cell & Melanoma Research, vol. 24, No. 1, Feb. 9, 2011, pp. 35-50.
Xanthe L. Strudwick, et al.; Combination of Low Calcium with Y-27632 Rock Inhibitor Increases the Proliferative Capacity, Expansion Potential and Lifespan of Primary Human Keratinocytes while Retaining their Capacity to Differentiate into Stratified Epidermis in a 3D Skin Model; PLOS ONE, vol. 10, No. 4, Apr. 13, 2015, pp. 1-12.
Netzlaff, F., et al.; The human epidermis models EpiSkin, SkinEthic and EpiDerm: An evaluation of morphology and their suitability for testing phototoxicity, irritancy, corrosivity, and substance transport; European Journal of Pharmaceutics and Biopharmaceutics, Elsevier Science Publishers B.V., Amsterdam, NL, vol. 60, No. 2, Jul. 1, 2005, pp. 167-178.
Tatiana Do Nascimento Pedrosa et al.; A new reconstructed human epidermis for in vitro skin irritation testing; Toxicology In Vitro; vol. 42, Aug. 1, 2017, pp. 31-37.
Carolina Motter Catarino, et al.; Skin corrosion test: a comparison between reconstructed human epidermis and full thickness skin

(56) References Cited

OTHER PUBLICATIONS models; European Journal of Pharmaceutics and Briopharmaceutics; vol. 125, Apr. 1, 2018, pp. 51-57.
Flaten, Goril Eide, et al; In vitro skin models as a tool in optimization of drug formulation; European Journal of Pharmaceutical Sciences, Elsevier Amsterdam, NL, vol. 75, Mar. 5, 2015, pp. 10-24.
Mathes Stephanie H., et al.; The use of skin models in drug development; Advanced Drug Delivery Reviews, Elsevier Amsterdam, NL., vol. 69, Apr. 1, 2014; pp. 81-102.
Gao X, Le X, Costa DB. The safety and efficacy of osimertinib for the treatment of EGFR T790M mutation positive non-small-cell lung cancer. Expert Rev Anticancer Ther. 2016;16:383-90.
Nicholson DW, Ali A, Thornberry NA, Vaillancourt JP, Ding CK, Gallant M, et al. Identification and inhibition of the ICE/CED-3 protease necessary for mammalian apoptosis. Nature. 1995;376:37-43. doi:10.1038/376037a0.
Peréz-Soler R, Saltz L. Cutaneous adverse effects with HER1/EGFR-targeted agents: is there a silver lining? J Clin Oncol. 2005;23:5235-46. doi:10.1200/JCO.2005.00.6916.
Reckamp KL, Giaccone G, Camidge DR, Gadgeel SM, Khuri FR, Engelman JA, et al. A phase 2 trial of dacomitinib (PF-00299804), an oral, irreversible pan-HER (human epidermal growth factor receptor) inhibitor, in patients with advanced non-small cell lung cancer after failure of prior chemotherapy and erlotinib. Cancer. 2014;120:1145-54.
Deshayes N. et al., "3D In vitro model of the re-epithelialization phase in the wound-healing process", Exp. Dermatol., 2018, vol. 27, N. 5, pp. 460-462, cf. abstract.
Robert C. et al., "RAF inhibition and induction of cutaneous squamous cell carcinoma", Curr. Opin. Oncol., 2011, vol. 23, N. 2, pp. 177-182, cf. abstract.
Faller, C., et al.; Predictive ability of reconstructed human epidermis equivalents for the assessment of skin irritation of cosmetics; Toxicology in Vitro 16, Issue 5, pp. 557-572—Dated Oct. 31, 2002.

\* cited by examiner

METHOD FOR EVALUATING THE EFFICACY OF A COMPOSITION IN REDUCING THE EFFECTS OF CANCER THERAPEUTICS ON SKIN

This application claims priority of the benefit of the filing of U.S. Provisional Application Ser. No. 62/950,624, filed Dec. 19, 2019, the contents of which are hereby incorporated by reference herein in their entirety.

FIELD OF THE INVENTION

The invention relates to methods to evaluate the potential of cancer therapeutics to produce skin related side effects. The present invention also relates to methods for evaluating the efficacy of a composition in reducing the effects of cancer therapeutics on skin.

BACKGROUND OF THE INVENTION

Oncology treatments targeting proliferative cells are frequently associated with Cutaneous Adverse Drug Reactions (CADR). CADRs involve 45-100% of patients receiving kinase inhibitors and can significantly affect the patients' quality of life. FIGS. 1a-1f are photographs showing examples of such cutaneous adverse reactions, including itch (FIG. 1a); dry, flaky, cracked skin (FIG. 1b); red rashes (FIG. 1c); sun sensitivity (FIG. 1d); face redness (FIG. 1e); and extra dry hands (FIG. 1f). CADRs often lead to dose modification or drug discontinuation disturbing the treatment protocol.

Oncology drugs impair keratinocyte proliferation and disrupt their differentiation. See Table 1 below and FIG. 2, which is a diagram showing healthy skin and damaged skin as a result of use of oncology drugs.

Growth Factor (VEGF) and the Platelet-Derived Growth Factor (PDGF) as well as the Human EGF Receptor 2 (HER2). Over-activation of these pathways in tumors leads to increased cell proliferation, angiogenesis and genetic abnormalities and suppression of apoptosis [3, 4]. Patients who initially respond to the TKi will generate resistance due to mutations within the 9 to 13 months after the beginning of their therapy, requiring a switch of the therapeutic regimen to address this appearance of such mutations [5, 6]. The first generations of TKi developed in the early 2000s, were followed by the development of the second and third generation of drugs to thwart the appearance of mutations in tumor cells. The third generation of EGFRi irreversibly inhibit EGFR despite the appearance of T790M mutation contributing to improved progression-free survival and reduction of CADR compared to standard chemotherapies [7, 8].

Chronic TKi treatments may also directly affect proliferative keratinocytes at the basal level of the epidermis, reducing cell growth rates, cell migration and promoting cell apoptosis, cell attachment, keratinocyte differentiation and pro-inflammatory cytokine expression [9, 10]. In this case, the resulting epidermal structure disturbance and skin barrier dysfunction could correlate with the clinically observed skin rash, pruritus, xerosis, hand-foot skin reaction, nail and hair alterations. Such CADR, also associated with pain and secondary infections, appear in 45-100% of patients receiving TKi and can significantly affect the patients' quality of life [5]. Medical examination by both dermatologists and oncologists to understand the nature and severity of the symptoms and the body surface area that is affected is necessary to prevent progression to more severe symptoms. Dose adjustment or even drug discontinuation could be required, leading to a disturbance of the oncology treatment

TABLE 1

| Compound | Family | Generation of drugs | Epidermis size | DSG-1 expression | IVL expression | FLG expression | Classification |
|---|---|---|---|---|---|---|---|
| Gefitinib | EGFRi | $1^{st}$ | Unchanged | Increased | Increased | Increased | Pro-differentiation |
| Erlotinib | EGFRi | $1^{st}$ | Decreased | Increased | Increased | Increased | Pro-differentiation |
| Afatinib | EGFRi | $2^{nd}$ | Decreased | Increased | Increased | Increased | Pro-differentiation |
| Lapatinib | EGFRi | $2^{nd}$ | Decreased | Increased | Increased | Increased | Pro-differentiation |
| Dacomitinib | EGFRi | $2^{nd}$ | Decreased | Increased | Increased | Increased | Pro-differentiation |
| Osimertinib | EGFRi | $3^{rd}$ | Unchanged | Unchanged | Unchanged | Unchanged | Unchanged |
| Sunitinib | VEGFRi | $1^{st}$ | Unchanced | Unchanged | Unchanged | Unchanged | Unchanged |
| Sorafenib | VEGFRi | $2^{nd}$ | Decreased | Unchanged | Unchanged | Decreased | Pro-proliferation |

The epidermis consists of a stratified epithelium, mainly composed of keratinocytes. It provides the first defense of the host against aggressors from the external environment, including pathogens, and prevents dehydration by controlling the rate of transcutaneous water loss. This barrier is highly dependent on the keratinocyte differentiation processes, from basal layer cells to terminal corneocytes in the stratum corneum. Oncology treatments target proliferative cells primarily using kinase inhibitors. Since the epidermal epithelium normally includes proliferative cells, it is reasonable to hypothesize that it also becomes a target of such therapies [1], a process that can lead to Cutaneous Adverse Drug Reactions (CADR) as consequence of defective epidermal differentiation, alteration of skin equilibrium and barrier dysfunction [2].

Tyrosine kinase inhibitors (TKi) target members of various growth factor receptors, such as the receptors of the Epidermal Growth Factor (EGF), the Vascular Endothelial protocol [11]. Paradoxically however, the appearance of skin rash during treatment is correlated with better survival of the patient [12].

U.S. Pat. No. 10,092,495 to Laboratoires Expanscience discloses a method for treating skin cancer, comprising administering an effective amount of at least one C7 sugar or derivative thereof.

U.S. Pat. No. 10,175,230 to Laboratoires Expanscience discloses a method for assessing the effectiveness of a C7 sugar or derivative thereof in the prevention and/or treatment of at least one deficiency of the skin barrier of a subject.

U.S. Published Application No. 20190242880 to Laboratoires Expanscience discloses methods for evaluating the in vitro efficacy of formulations in preventing the effects of dehydration on children's skin.

An object of the invention is to deliver solutions for an integrated therapeutic approach aimed to improve the quality of life and provide optimal drug therapy outcomes for patients undergoing drug treatment.

SUMMARY OF THE INVENTION

Since the EGFR pathway is pivotal for epidermal keratinocytes, it is reasonable to hypothesize that Epidermal Growth Factor Receptor inhibitors (EGFRi) targeting carcinomas also affect these cells and therefore interfere with the epidermal structure formation and skin barrier function.

To test this hypothesis, the effects of EGFRi and Vascular Endothelial Growth Factor Receptor inhibitors (VEGFRi) at therapeutically relevant concentrations (3, 10, 30, 100 nM) were assessed on proliferation and differentiation markers of human keratinocytes in a novel 3D micro-epidermis tissue culture model.

EGFRi directly affects basal keratinocyte growth leading to tissue size reduction and switching keratinocytes from a proliferative to a differentiative phenotype as evidenced by decreases in Ki67 staining and increases in filaggrin, desmoglein-1 and involucrin expression. These effects lead to skin barrier impairment which can be observed in a reconstructed human epidermis model showing a decrease in trans-epidermal water loss rates. On the other hand, pan-kinase inhibitors mainly targeting VEGFR barely affect keratinocyte differentiation and rather promote a proliferative phenotype.

This study contributes to the mechanistic understanding of the clinically observed CADR during therapy with EGFRi. These in vitro results suggest a specific mode of action of EGFRi by directly affecting keratinocyte growth and barrier function.

Oncology therapy and particularly EGFRi directly affects basal keratinocyte growth leading to tissue size reduction and switching keratinocytes from a proliferative to a differentiative phenotype. Such processes contribute to compromised barrier and skin impairment.

It is believed that supporting skin barrier can help ameliorate therapy-related skin rashes/conditions.

An object of the invention is to deliver solutions for an integrated therapeutic approach aimed to improve the quality of life and provide optimal drug therapy outcomes for patients undergoing drug treatment.

In accordance with the invention, a reconstructed human epidermal (RHE) model which can functionally reproduce barrier compromise due to oncology treatment was used to test compositions that can abrogate the effect cancer agents have on skin barrier structure and function. FIG. 3a is a photograph of the model and FIG. 3b is a diagram showing assessment of barrier function and biomolecular markers.

To assess the effects of such therapy molecules on the epidermis, keratinocytes were grown in the presence of kinase inhibitors during 3 days with high calcium concentration to induce keratinocyte differentiation and generate a 3D-stratified differentiated epidermis. Drug impact on the epidermis development was assessed via different keratinocyte markers including:

Ki-67, an universally expressed protein among proliferating cells and absent in the quiescent cells [13];
Filaggrin, a filament-associated protein that binds to keratin fibers and is a marker of terminal differentiation [14];
Desmoglein-1, a component of desmosomes and differentiation marker expressed in all epidermal layer above the basal layer [15]; and
Involucrin, an early differentiation marker expressed in the spinous and granular layers and a protein precursor of the epidermal cornified envelope [16].

DETAILED DESCRIPTION OF THE INVENTION

Materials and Methods

Determination of Unbound Plasma Drug Concentration

Figure 1A:
FIGS. 1a-1f are photographs showing examples of such cutaneous adverse reactions, including itch (FIG. 1a); dry, flaky, cracked skin (FIG. 1b); red rashes (FIG. 1c); sun sensitivity (FIG. 1d); face redness (FIG. 1e); and extra dry hands (FIG. 1f).
Figure 1B:
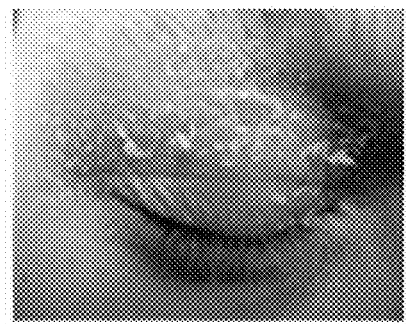
Figure 1C:
Figure 1D:
Figure 1E:
Figure 1F:
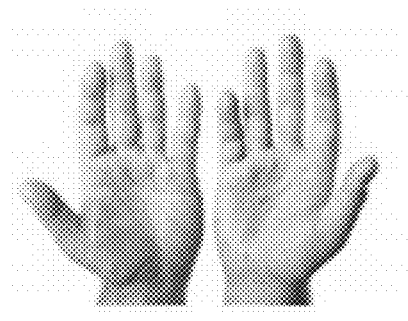
Figure 2:
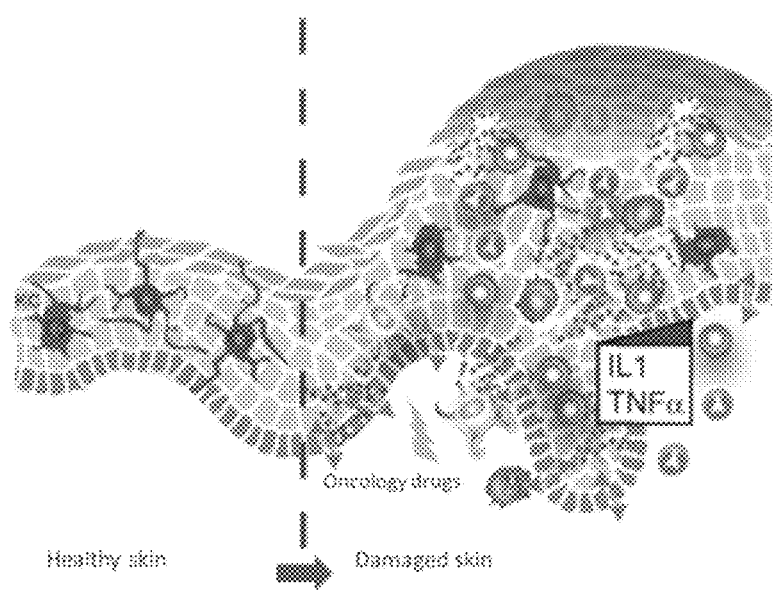
FIG. 2 is a diagram showing healthy skin and damaged skin as a result of use of oncology drugs.
Figures 3A, 3B:
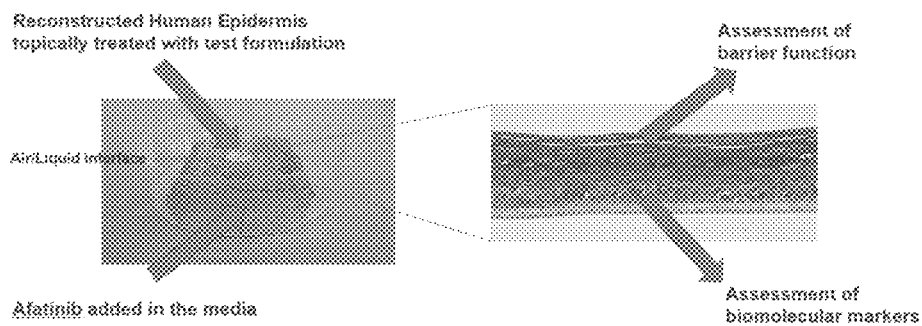
FIG. 3a is a photograph of the reconstructed human epidermal (RHE) model and FIG. 3b is a diagram showing assessment of barrier function and biomolecular markers.
Figures 4A, 4B, 4C, 4D, 4E, 4F:
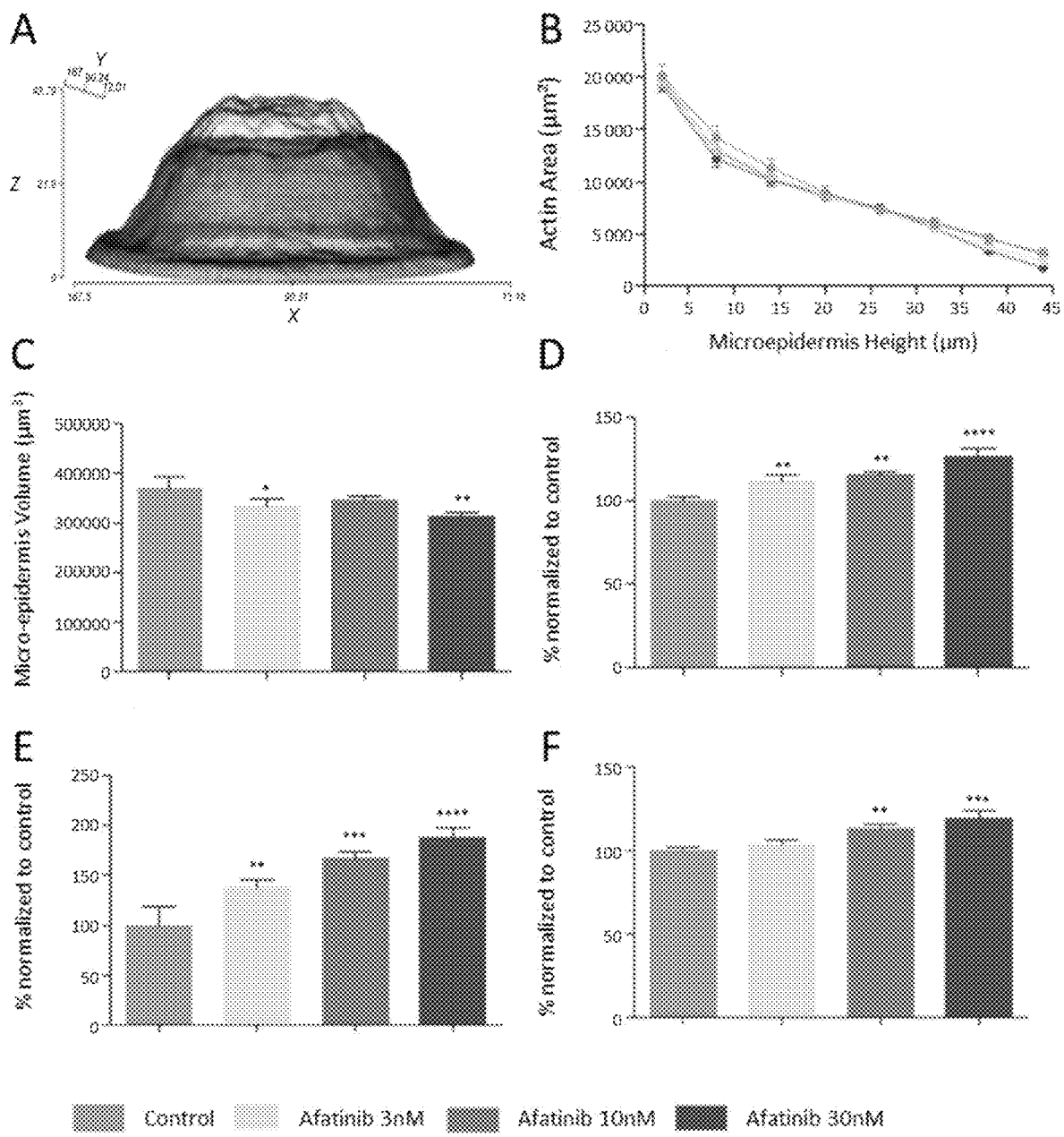
FIGS. 4a to 4f (shown as A-F, respectively) are graphs showing that afatinib decreases the size of the epidermis and increases skin differentiation markers. Micro-epidermises were treated with afatinib at 3, 10, 30 nM. Drugs and concentrations effect on microepidermis were assessed with different parameters (a) Micro-epidermis volume incubated with afatinib 30 nM; (b) actin expression intensity; (c) microepidermis volume; (d) desmoglein-1 expression; (e) involucrin expression; and (f) filaggrin expression. * $p<0.05$,  $p<0.01$, * $p<0.001$.

In vitro drug exposure ranges at therapeutically relevant concentrations (3-100 nm) were selected rather than micromolar to millimolar range previously used in literature [17, 18]. These concentrations appeared to be more relevant to study the long-term effect of treatments on the epidermis. Using published research, the maximal drug concentration in plasma following a single daily-recommended dose of drug in a healthy patient was identified. The percentage of unbound fraction to plasma protein was identified or calculated using $C_{max}$ plasma concentration and the percentage of unbound fraction in the plasma. Plasma protein binding of the TKi from the study ranged from 0.3 to 5%. The highest unbound plasma concentration is for erlotinib (80 nM; Togashi et al. 2010) and the lowest for dacomitinib (0.42 nM; Giri et al. 2015). EGFRi equilibrium dissociation constants ($K_D$) have been reported by Klaeger et al. [19]. It was possible to compare the EGFRi used in this study. EGFRi drug potencies, ranging from afatinib with a $K_D$ of 2 nM and erlotinib, a first-generation drug, with a $K_D$ of 2,164 nM, (Table 2). Surprisingly, the potency of osimertinib, a third generation of EGFRi, was not decreased compared to second-generation drug such as the afatinib, lapatinib and dacomitinib. VEGFRi $K_D$ were compared using literature.

TABLE 2

| | | | Biological Effect | | |
|---|---|---|---|---|---|
| Name | Family | Generation of drug | Mode of action | Major Skin Effect | Indication |
| Sunitinib | VEGFRi | 1/2 | Reversible | Palmoplantar erythroderma | Gastrointestinal stromal tumor; Renal cell carcinoma; Pancreatic neuroendocrine tumor |
| Sorafenib | VEGFRi | 2/2 | Reversible | Rash | Liver cell carcinoma; carcinoma of thyroid; Renal cell carcinoma |
| Gefitinib | EGFRi | 1/3 | Reversible | Papulo-pustular rash | NSCLC |
| Erlotinib | EGFRi | 1/3 | Reversible | Papulo-pustular rash | NSCLC; Pancreatic cancer |
| Afatinib | EGFRi | 2/3 | Irreversible | Rash | NSCLC with epidermal growth factor receptor (EGFR)-activating mutations |
| Lapatinib | EGFRi | 2/3 | Reversible | Rash | HER2 positive carcinoma of breast |
| Dacomitinib | EGFRi | 2/3 | Irreversible | Rash | NSCLC with epidermal growth factor receptor (EGFR)-activating mutations |
| Osimertinib | EGFRi | 3/3 | Irreversible | Papulo-pustular rash | NSCLC with T790M-L858R mutation positive |
| Osimertinib | EGFRi | 3/3 | Irreversible | Papulo-pustular rash | NSCLC with T790M-L858R mutation positive |

| Name | Chemical structure | MW (g/mol) | Daily dose (mg/day) | Cmax (nM) | Kd (nM) | Unbound fraction (%) | Unbound concentration (nM) | References |
|---|---|---|---|---|---|---|---|---|
| Sunitinib | | 398.474 | 50 | 75* | VEGFR2: 1.5** | 5%* | 2.5* | *Rais 2012 **Fabian et al. 2005 |
| Sorafenib | | 464.825 | 200 | 8175* | VEGFR2: 59** | 0.29% | 23.6* | *Villarroel 2012 **Davis et al. 2011 |
| Gefitinib | | 446.902 | 250 | 355.8* | EGFR: 413*** | 3.4%** | 1 | *Swaisland 2005 **Li 2006 ***Klager et al. 2017 |
| Erlotinib | | 393.436 | 150 | 1599* | EGFR: 2164** | 5% | 79.95* | *Togashi 2010 **Klaeger et al. 2017 |
| Afatinib | | 485.937 | 50 | 32* | EGFR: 2** | 5%* | 1.6 | *Wind 2017 *Klaeger et al. 2017 |
| Lapatinib | | 581.058 | 250 | 516.3* | EGFR: 51** | 1%* | 5.16* | *Hudachek 2013 **Klaeger et al. 2017 |
| Dacomitinib | | 469.95 | 45 | 177.5* | EGFR: 5** | 0.24% | 0.425* | *Giri 2015 *Klaeger et al. 2017 |

TABLE 2-continued

| Osimertinib | 499.619 | 80 | 627 | EGFR: 155** | 1.32%* | 8.2764 | *Reddy 2018 **Klaeger et al. 2017 |

Biological and activity data of VEGFRi and EGFRi. Biological effect data were compiled from the information provided by the web site drugcentral.org (accessed in November 2019). As "major skin effect" present here is the most frequent cutaneous adverse reaction reported by the FDA Adverse Event Reporting System. NSCLC: non-small cell lung cancer. Drug $K_D$ and the determination of plasma concentration after a single dose administration in human are reported here from literature. Data from Klaeger et al. 2017 were used to compare drug $K_D$ for EGFRi. Unbound plasma drug fraction was determined as a concentration at nanomolar scale in the literature.

Drug Preparation

The selected drugs corresponding to plasma relevant concentrations (3, 10, 30, 100 nM) following administration of a single dose and at 1 µM drug concentration were prepared from a 10 mM stock solution dissolved in DMSO. Consequently, the final DMSO concentration was 0.01% for the highest concentration 1 µM. Vehicles were composed of the same DMSO volume as the drug treatment. Acetaminophen was used as negative control in the same proportion of DMSO.

Assessment of Skin Barrier Function

The effect of drugs on the skin barrier function was assessed by measuring trans-epidermal water loss (TEWL) rates on SkinEthic™ Reconstructed Human Epidermis (RHE) model (Episkin, Lyon, France) using Tewitro® TW 24 (Courage+Khazaka electronic GmbH, Köln, Germany). This instrument allows 24 simultaneous measurements on RHE. TEWL was analyzed at 33° C. in an incubator. Measurement was performed after 1 h TEWL stabilization and 5 min average of TEWL measurement was performed. Experiments were performed in triplicate and results were normalized to 100% to the TEWL of the control. SDS 0.5% in PBS was added at the surface of the RHE to damage the epidermis structure and consequently increase the TEWL (positive control). Petrolatum, a highly hydrophobic hydrocarbon, water-repelling and insoluble in water was used to block water evaporation at the RHE surface (negative control). Afatinib was added at 100 nM in the media and renewed every 2 or 3 days to simulate chronic drug exposure. DMSO was used in the same proportion in the vehicle.

SkinEthic™ RHE (Episkin, Lyon, France), is an in vitro reconstructed human epidermis from normal human keratinocytes cultured on an inert polycarbonate filter at the air-liquid interface, in a chemically defined medium. This model exists at different stages of maturity. This model is histologically similar to in vivo human epidermis. See https://www.episkin.com/SkinEthic%20RHE.

Transepidermal Waterloss Measurement in Cultured Skin Samples

The Tewitro® TW 24 is a device that measures water evaporation from cultured tissue sets (wells in a plate with medium) in up to 24 wells simultaneously. See https://www.courage-khazaka.de/en/16-wissenschaftliche-produkte/alle-produkte/159-tewitro-e.

EpiScreen™ Protocol

Human epidermal keratinocytes cells (HPEKs) from a juvenile Caucasian donor (CellnTec, Switzerland) are cultured in flasks in proliferation medium. Keratinocytes are seeded at passage 6 into EpiScreen™ (Abzena, Cambridge, UK) plates containing collagen 1 coated disc micropatterns (CYTOO, Grenoble, France). Four hours later, unattached cells are washed off and a high calcium medium is added to induce keratinocytes differentiation. The day after, keratinocytes are treated with screening compounds, and Trichostatin A is added at 0.3 µM as an internal positive control. After three days of treatment, micro-epidermises are fixed with a formalin solution 10% for 30 minutes, then permeabilized with 0.1% Triton. Several immunostainings are performed: actin (Acti-Stain 555, PHDH1, Cytoskeleton), nuclei (Hoechst, H3570, Invitrogen), and one biomarker of interest per well either anti-involucrin (HPA055211, Sigma), anti-filaggrin (HPA030189, Sigma) or anti-desmoglein-1 (HPA022128, Sigma). Antibodies are added overnight at 4° C. before staining with secondary antibody, anti-rabbit 488 (711-545-152, Jackson) for 2 hours at room temperature.

Images Acquisition and Analysis

Images of each well are acquired with the Operetta HCS platform (Perkin Elmer, Waltham, MA, USA) using a ×10 objective in confocal mode in eight z-planes from 2 µm to 44 µm in steps of 6 µm in each of the 3 channels: actin, nuclei, and one biomarker of interest. The first step of the image analysis consists in detecting micro-epidermis structures on the first z-plane by segmenting the actin staining. Micro-epidermis structures are validated based on several area and roundness min and max criteria. Then, the area of each biomarker staining is measured inside the valid micro-epidermis masks through each z-plane. For all homogeneous biomarker staining, their intensity through the different planes is measured.

Reconstruction of 3D Micro-Epidermis Images

Based on 50 to 80 micro-epidermis structures per well, an "average" 3D image is built up to represent the micro-epidermis phenotype in this well. Micro-epidermis structures are detected using the actin staining in the first z-plane and selected based on area and roundness criteria.

The actin network of each micro-epidermis is analyzed in each z-plane in order to determine the average 3D structure edges. The biomarker intensity is measured in each z-plane for each structure, and then averaged with the other results generated in the same well. Based on the data generated in the two previous steps, an average 3D reconstruction image is generated. It consists of a meshwork that delimits the structure edges, and a color scaled volume that corresponds to the biomarkers distribution and expression.

Viability and Proliferation Assay

The Water-Soluble Tetrazolium Salts (WST-8) Colorimetric Cell Proliferation Kit (Promokine, Heidelberg, Germany) provides a rapid and sensitive way to quantify proliferation and cell viability. Cell proliferation causes an increase in the amount of formazan dye formed that can be quantified by measuring the absorbance of the dye solution at 440 nm using a microtiter plate reader (Perkin Elmer EnVision 2103 Multilabel Reader, Waltham, MA, USA). Cellular proliferation induces an increase in the activity of mitochondrial dehydrogenases, which cleaves the tetrazolium salt WST-1 into formazan. 15,000 Keratinocytes per well were seeded on 96-well plate, once confluence reach, drug concentration used were +/−½ log of the plasmatic concentration. 10 µl of Colorimetric Cell Viability Kit is added and completed with 360 µl of culture media, results were read after 4 h at 450 nm to determine cell viability. Results were obtained with 6 donors of keratinocytes in 2 experiments Caspase-3 Fluorometric Assay Kit The kit (biotium, Fremont, CA, USA) provides a homogenous assay system for fast and highly sensitive detection of caspase-3 activity by fluorescence in enzymatic reaction or mammalian cells. The fluorogenic substrate (Ac-DEVD) 2-R110 contains two DEVD (Asp-Glu-Val-Asp) tetrapeptides and is completely hydrolyzed by the enzyme in two successive steps. Cleavage of the first DEVD peptide results in the monopeptide Ac-DEVD-R110 intermediate, which has absorption and emission wavelengths similar to those of R110 (Ex/Em=496/520 nm) but has only about 10% of the fluorescence of the latter. Hydrolysis of the second DEVD peptide releases the dye R110, leading to a substantial fluorescence increase. Keratinocytes were plated at 15,000 cells per well in 100 µl of medium in a 96-well black microplate. They were allowed to attach and grow overnight in a 37° C., 5% CO2 incubator. They were then treated for 20 h with a 1:2 dilution series of staurosporine, a caspase 3 inducer [20]. Imaging was performed on Perkin Elmer EnVision 2103 Multilabel Reader using an excitation wavelength of 490 nm and emission wavelength of 535 nm. Cells were incubated at room temperature for 15 min, protected from light. Results were obtained with 6 donors of keratinocytes in 2 experiments Statistics Results are expressed as means+/−SD. All experiments were performed at least in triplicate. Statistical analysis was performed using one-way analysis of variance (ANOVA) and Student's t-test. Statistical significance for the difference between the two groups was accepted at the level of $p<0.05$.

Results

The effect of 8 oncology molecules, selected from first generation EGFRi and pan-kinase inhibitors which mostly target VEGFR and second and third generation therapies targeting main mutations relating to first generation treatment resistance, were assessed in vitro using a 3D micro-epidermis model. The drug incubation concentrations (3, 10, 30, 100 nM) were selected to reflect the clinically relevant (unbound) drug exposures (Table 2). The drug impact was assessed by analysis of tissue size and keratinocyte proliferation using Ki-67 staining and keratinocyte differentiation using filaggrin, desmoglein-1 and involucrin staining.

Increased micro-epidermis size and Ki-67 staining with a concomitant decreased of filaggrin, desmoglein-1 and involucrin expression were considered as a pro-proliferation effect of the tested molecule. On the other hand, a pro-differentiation effect was defined as a decrease of both the micro-epidermis size and Ki-67 staining and an increase of filaggrin, desmoglein-1 and involucrin expression.

Pan-Kinase Inhibitors Barely Impact the Micro-Epidermis Structure and Differentiation Markers Sunitinib has no impact on the epidermis size and sorafenib strongly decreases the size of the epidermis. Both pan-kinase inhibitors do not impact the desmoglein-1 and involucrin protein expression and significantly decrease filaggrin protein expression. Of note, this effect of pan-kinase inhibitors was achieved at 100 nM, lower concentrations did not impact the markers followed in the study. Sunitinib was the only TKi assessed that did not shown any toxicity at the highest concentration tested (1 µM). These results indicate that VEGFRi have a pro-proliferation effect on the keratinocytes.

EGFRi Affect Epidermal Structure and Differentiation Markers

Most of the EGFRi tested (Table 3), including afatinib, lapatinib, and dacomitinib, showed an effect on desmoglein-1, involucrin and filaggrin expression in a dose-dependent manner. Gefitinib increased in a dose-dependent manner only the expression of desmoglein-1. Erlotinib and osimertinib did not affect the expression of the junction proteins. For all EGFRi tested, the epidermal toxicity evaluated at 1 µM was significant, interfering with the epidermal development, to the point that no tissue was available for further data analysis. (Table 3) At unbound plasma drug concentrations 3, 10, and 30 nM, all first and second generation EGFRi showed a decrease in keratinocyte proliferation, micro-epidermis size and an increase of the desmoglein-1, involucrin and filaggrin protein expression, evidence of a pro-differentiation effect.

TABLE 3

| Compound | Family | Drugs Gen | Epidermis size | DSG1 expression | IVL expression | FLG expression | Dose in response | Toxicity at 1 µM | Classification |
|---|---|---|---|---|---|---|---|---|---|
| Sunitinib | VEGFRi | 1st | Unchanged[4] | −16%[4] | 0%[4] | −12%[3] | No | No | Pro-proliferation |
| Sorafenib | VEGFRi | 2nd | Decreased[2] | −9%[4] | 2%[4] | −28%[1] | No | Yes | Pro-proliferation |
| Gefitinib | EGFRi | 1st | Unchanged[4] | −15%[7] | 23%[4] | 5%[4] | Yes (DSG) | Yes | Pro-differentiation |
| Erlotinib | EGFRi | 1st | Decreased[1] | 1%[4] | 22%[6] | 10%[4] | No | Yes | Pro-differentiation |
| Afatinib | EGFRi | 2nd | Decreased[2] | 87%[5] | 12%[5] | 19%[5] | Yes (DSG, IVL, FLG) | Yes | Pro-differentiation |
| Lapatinib | EGFRi | 2nd | Unchanged[4] | 29%[6] | 30%[6] | 20%[6] | Yes (DSG, IVL, FLG) | Yes | Pro-differentiation |
| Dacomitinib | EGFRi | 2nd | Unchanged[4] | 54%[5] | 60%[5] | 31%[7] | Yes (DSG, IVL, FLG) | Yes | Pro-differentiation |

TABLE 3-continued

| Compound | Family | Drugs Gen | Epidermis size | DSG1 expression | IVL expression | FLG expression | Dose in response | Toxicity at 1 µM | Classification |
|---|---|---|---|---|---|---|---|---|---|
| Osimertinib | EGFRi | 3$^{rd}$ | Unchanged[4] | 7%[4] | 7%[4] | 2%[4] | No | Yes | Unchanged |
| Acetaminophen | Neg control | N/A | Unchanged[4] | 18%[4] | 4%[4] | −5%[4] | No | Yes | Unchanged |

[1]Decreased p < 0.001;
[2]Decreased p < 0.01;
[3]Decreased p < 0.05;
[4]Non-significant p > 0.05;
[5]Increased p < 0.001;
[6]Increased p < 0.01;
[7]Increased p < 0.05

Micro-Epidermis Physiology is Impaired Following Exposure to EGFRi and VEGFRi.

Size of the epidermis and the expression of the protein junction desmoglein-1 (DSG1), involucrin (IVL) and filaggrin (FLG) was assessed by immunostaining and compared to untreated control. Drugs were classified by family and drug generation. Dose responses were determined by comparison of the variation of protein expression at 3, 10, 30 nM for EGFRi and 3, 10, 30, 100 nM for the VEGFRi. * p<0.05 at 30 nM (EFGRi) or 100 nM (VEFGRi);  p<0.01 at 30 nM (EFGRi) or 100 nM (VEFGRi) and * p<0.001 at 30 nM (EFGRi) or 100 nM (VEFGRi).

Interestingly, the osimertinib, a third generation of EGFRi developed to target drug resistance cells but also to provide better drug tolerance, was the only EGFRi which did not show any impact on all parameters except cell toxicity at the higher concentration (1 µM).

Afatinib Affects Keratinocyte Protein Expression, Viability and Proliferation

Afatinib (FIGS. 4a to 4f) treatment resulted in significantly decreased epidermal volume in the 3D reconstructed micro-epidermis model compared to vehicle. Involucrin and desmoglein-1 expression were significantly increased at 3, 10, 30 nM in a dose-dependent manner and filaggrin expression was significantly increased at 10 nM and 30 nM in a dose-dependent manner. A higher drug concentration above 1 µM was toxic leading to epidermal necrosis.

The effect of Afatinib on the epidermal barrier function was assessed on RHE models by measuring the rate of TEWL. Addition of petrolatum (negative control) led to a significant decrease of the TEWL rate by 48%, 77%, 75% and 82% respectively on day 1, 2, 5, and 7 following application, compared to untreated control. The surfactant sodium dodecyl sulfoxide (SDS, at 0.5% used as positive control) significantly increased the TEWL rate by 98% 77% and 58% respectively on days 1, 2, and 5 following application. On day 7 following SDS application, a non-significant increase of the TEWL rate was observed. Afatinib significantly increased the rate of TEWL by 22% on day 2, while on days 5 and 7 no significant change was observed.

Further results show that afatinib had a significant effect on cell viability (FIG. 5a) in a dose-dependent manner. On the other hand, afatinib did not show any effect at 2.59 nM and 25.89 nM on cell apoptosis (FIG. 5b). Taken together these results show that afatinib impairs keratinocyte viability and proliferation in the micro-epidermis model, but it does not induce keratinocyte apoptosis.

Acetaminophen used as control showed no effect on any of the measured parameters including cell toxicity at 1 µM.

Capacitance and trans-epidermal water loss (TEWL) rates were measured to assess the ability of AVEENO® Restorative Skin Therapy Itch Relief Balm and AVEENO® Restorative Skin Therapy Oat Repairing Cream to counteract the effect of afatinib treatment on skin barrier function.

36 µl of the balm or cream formulation is added and spread on the whole surface of the RHE with a pipette Pasteur. The balm or cream formulation is then stabilized for at least 48 h in a dried incubator to remove water contents so as not to disturb the TEWL measurement.

Drug in the media is added in accordance with the protocol set forth above and the RHE is incubated. In case of combination of both drug and formulation, drug needs to be added at D+1 after the formulation, in order to stabilize the formulation on the top of the RHE.

Figure 7:
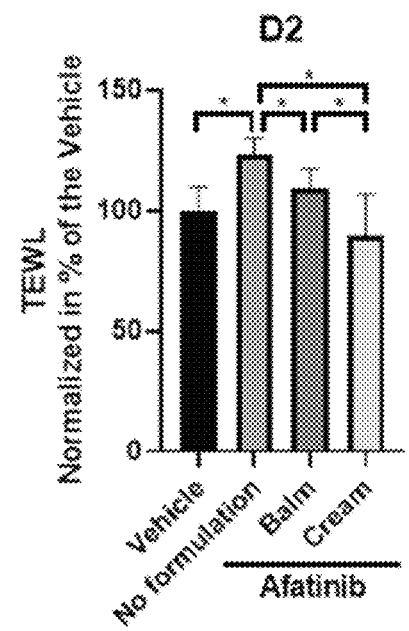
FIG. 7 is a graph showing the effect of AVEENO® Restorative Skin Therapy Itch Relief Balm and AVEENO® Restorative Skin Therapy Oat Repairing Cream on skin barrier function after treatment with afatinib.

The balm contains the following ingredients:
Active Ingredient: Pramoxine HCl (0.5%)
Inactive Ingredients: water, glycerin, distearyldimonium chloride, petrolatum, isopropyl palmitate, cetyl alcohol, panthenol, dimethicone, *Avena sativa* (Oat) kernel flour, benzyl alcohol, cetyl hydroxyethylcellulose, chlorphenesin, steareth-20, aloe barbadensis leaf extract, sodium chloride, *Avena sativa* (oat) kernel extract The cream contains the following ingredients:
Water, Glycerin, Distearyldimonium Chloride, Petrolatum, Isopropyl Palmitate, Cetyl Alcohol, Panthenol, Dimethicone, *Avena Sativa* (Oat) Kernel Flour, Benzyl Alcohol, Steareth-20, Aloe Barbadensis Leaf Extract, Sodium Chloride, *Avena Sativa* (Oat) Kernel Extract The results are shown in FIG. 7.

Discussion

The emergence of the TKi in the treatment of cancer has successfully increased the five-year patient survival rate. EGFRi and VEGFRi have led to considerable progress in the treatment of various solid tumors since their introduction and the new generation has considerably increased their efficiency [21]. By targeting proliferative cells, oncology treatments can provoke CADR that potentially disrupt the treatment protocol and impact the patient quality of life [7]. The mechanisms leading to CADR are still poorly understood. Thus far, the effects of TKi on keratinocytes are still unknown and published research has dealt only with relatively high drug concentrations without considering the relevant plasma concentration affecting keratinocytes in a chronic manner. The results presented in this work provide for the first time a better understanding of the mode of action of oncology treatment on the pathophysiology of CADR.

Sunitinib and sorafenib, two Pan kinase inhibitors mainly targeting VEGFRi have unbound plasmatic fractions of 2 nM and 23.6 nM respectively with equilibrium dissociation constants ($K_D$) of 1.5 nM and 59 nM. The study on micro-epidermis performed in the same concentration range had no effect on the epidermal structure, only filaggrin expression was significantly increased for both Sunitinib and Sorafenib. Of note, sunitinib was the only drug in our panel that did not lead to keratinocyte toxicity at 1 µM. It is conceivable that the negative effects of VEGFRi on skin may potentially arise from an impairment of the skin vascularization disturbing keratinocyte growth [22]. The absence of effect using sorafenib at the higher concentration could confirm our hypothesis.

In contrast, EGFRi clearly affect keratinocyte growth at the basal layer leading to a decrease of the epidermal volume in the micro-epidermis model. Afatinib leads to a decreased epidermal volume at 3 nM. On the other hand, afatinib increased the expression of desmoglein-1, involucrin and filaggrin, indicating that EGFRi promote late terminal differentiation while decreasing keratinocyte proliferation at the basal layer.

Osimertinib had surprisingly no impact on epidermis development. This data taken together with an high $K_D$ value (155 nM) (Table 2) compared to previous drug generation can be explained by the fact that osimertinib targets main mutations (T790 and C797S) generated after long period treatment with first and second generation drugs. Consequently, osimertinib exhibits a higher inhibition of the mutated receptor compared to the wild type receptor and barely affects the micro-epidermis development in this study.

Afatinib is an irreversible inhibitor of EGFRi associated with the lowest unbound plasma concentration, $C_{max}$ and $K_D$ of the panel. See structure below.

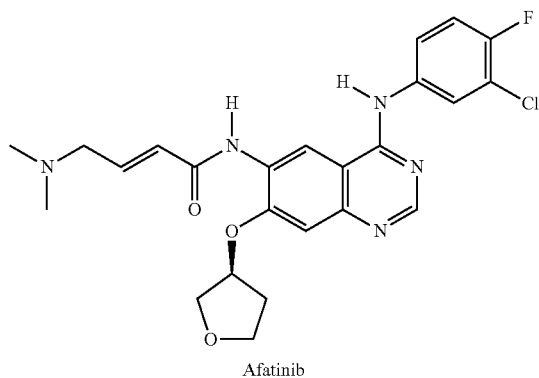 [SMILES: CN(C)C/C=C/C(=O)Nc1cc2c(Nc3ccc(F)c(Cl)c3)ncnc2cc1O[C@H]1CCOC1]

Afatinib

Afatinib impacts all parameters of the study (i.e. epidermis size, skin barrier markers). Consequently, the dose response of afatinib (FIGS. 4a to 4f) at 3, 10 and 30 nM corresponding to the range of the unbound plasma concentration to determine keratinocyte growth in the epidermal development was examined. The micro-epidermis size was significantly reduced at 3 and 30 nM. Involucrin, desmoglein-1 and filaggrin were moreover all increased in a dose-dependent manner. Taken together, afatinib affects all markers studied by decreasing keratinocyte proliferation at the basal layer and inducing keratinocyte differentiation, an effect that has a measurable impact on skin barrier function.

Figure 5A:
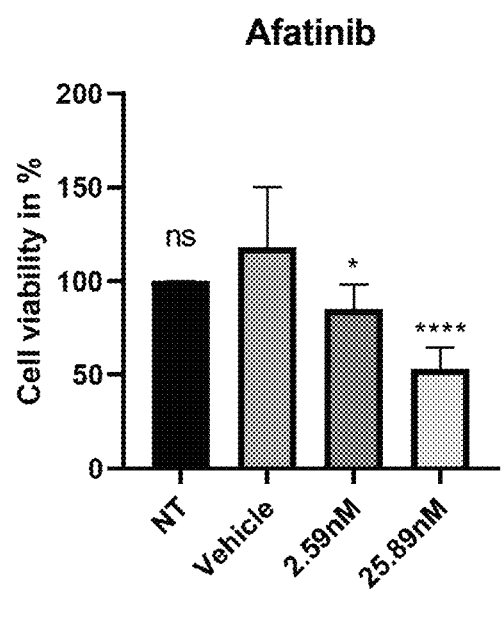
FIGS. 5a and 5b are graphs that show the effect that afatinib has on cell viability (FIG. 5a) and on cell apoptosis (FIG. 5b). A) Keratinocyte viability decreases following exposure to afatinib. B) Afatinib does not induce apoptosis in keratinocytes. Keratinocytes were exposed for 24 h to each condition shown. Percentages represent the relative effect compared to vehicle. Staurosporine at 1 µM was used as positive control and correspond to 100% of cell apoptosis. Post-hoc Dunett's test * $p<0.05$, **** $p<0.0001$.
Figure 5B:
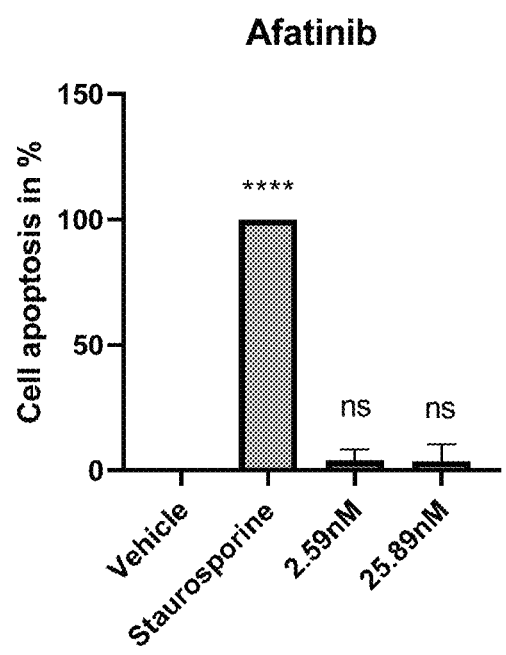
Figure 6:
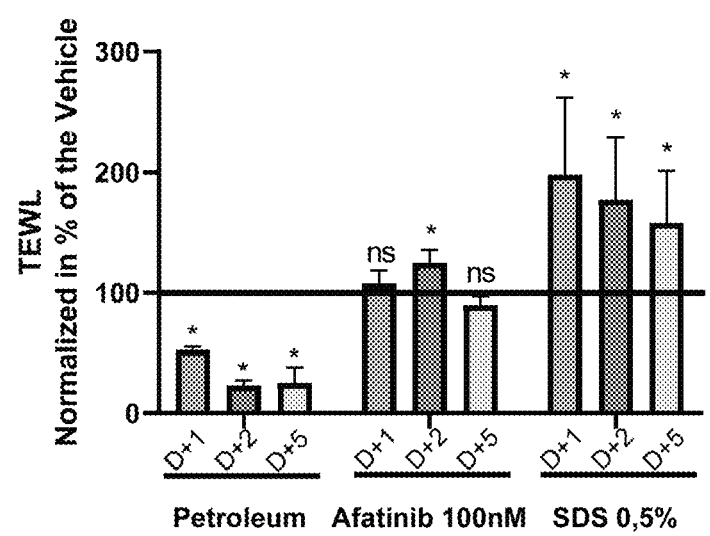
FIG. 6 is a graph showing that RHE skin barrier function is deteriorating on day 2 of afatinib treatment. Skin barrier function was assessed by measuring the rate of trans epidermal water loss. Topical application of petrolatum on the RHE was used as negative control and topical exposure to a 0.5% SDS solution on the RHE was used as positive control.

Functional consequences of afatinib were investigated on the barrier function on reconstituted epidermis (FIGS. 5a and 5b). TEWL rates were significantly increased on day two. This result demonstrates that afatinib quickly affects skin barrier. Restoration of the TEWL values on day 5 following RHE exposure to afatinib could be due to afatinib-induced increase in the expression of filaggrin, desmoglein-1 and involucrin reported above. Clinically CADR symptoms have been reported to appear within the first days of the treatment and then disappear, only to reappear one to two months after continuous exposure to oncology drugs [24]. Our results indicating that afatinib induces an early increase in TEWL is in agreement with this clinical observation. Late manifestation of CADRs may relate to the decreased proliferation and cellular fatigue.

Further analysis was performed to elucidate afatinib effect on keratinocytes. The apoptotic activity of keratinocytes was not affected at either dose tested indicating that size reduction of the epidermis is not related to apoptosis. All these data suggest that CADRs are provoked by a decreased keratinocyte proliferation impairing skin regeneration and leading to epidermal size reduction rather that by inducing keratinocyte apoptosis in the epidermis.

Taken together, upon drug exposure keratinocytes undergo a rapid switch from a proliferative to a differentiative phenotype as a sort of response to a damaging insult. Over a longer period of exposure, the decrease of keratinocyte progenitors able to renew the epidermis could explain the appearance of rashes, dry skin that becomes evident after a few weeks of drug exposure.

Finally, the new generation of oncology treatment using immunotherapies has also reported important CADRs similar to treatments with small molecules targeting TKi. Consequently, a better understanding of the effects of such drugs on skin physiology is still necessary to manage such disorders for a better quality of life for the patient.

CONCLUSION

The effect of oncology therapy molecules at concentrations below the toxic level on epidermal development in vitro was evaluated. These relevant concentrations allow us to demonstrate that oncology treatment impaired keratinocyte growth and consequently affect skin barrier. These results underlie the need of prevention to support the skin barrier function during oncology therapy and consequently decrease the appearance of such CADRs.

It will be understood that, while various aspects of the present disclosure have been illustrated and described by way of example, the invention claimed herein is not limited thereto, but may be otherwise variously embodied according to the scope of the claims presented in this and/or any derivative patent application.

REFERENCES (EACH OF THE REFERENCES LISTED BELOW ARE INCORPORATED BY REFERENCE IN THEIR ENTIRETY HEREIN.)

CADR Cutaneous adverse drug reactions
Tki Tyrosine kinase inhibitors
EGFRi Epidermal Growth Factor Receptor inhibitors
VEGFRi Vascular Endothelial Growth Factor Receptor inhibitors
3D 3-Dimensional
HER2 Human EGF Receptor 2
Cmax Concentration maximum
Kd Dissociation constant
nM Nano Molar
UM Micro Molar
DMSO Dimethylsulfoxyde
TEWL Transepidermal water loss
RHE Reconstructed Human Epidermis SDS Sodium Dodecyl Sulfate
PBS Phosphate-buffered saline
WST-8 Water-Soluble Tetrazolium Salts
SDS Standard deviation
MW Molecular Weight
NSCLC Non-small-cell lung carcinoma
DSG1 Desmoglein
IVL Involucrin
FLG Filaggrin

REFERENCES

1. Peus D, Hamacher L, Pittelkow M R. EGF-receptor tyrosine kinase inhibition induces keratinocyte growth arrest and terminal differentiation. J Invest Dermatol. 1997; 109:751-6.
2. Tischer B, Huber R, Kraemer M, Lacouture M E. Dermatologic events from EGFR inhibitors: the issue of the missing patient voice. Support Care Cancer. 2017; 25:651-60. doi: 10.1007/s00520-016-3419-4.
3. Kwak E L, Shapiro G I, Cohen S M, Becerra C R, Lenz H-J, Cheng W-F, et al. Phase 2 trial of afatinib, an ErbB family blocker, in solid tumors genetically screened for target activation. Cancer. 2013; 119:3043-51. doi: 10.1002/cncr.28120.
4. Hanahan D, Weinberg R A. Hallmarks of cancer: the next generation. Cell. 2011; 144:646-74. doi: 10.1016/j.cell.2011.02.013.
5. Lacouture M E. Mechanisms of cutaneous toxicities to EGFR inhibitors. Nat Rev Cancer. 2006; 6:803-12.
6. Gao X, Le X, Costa D B. The safety and efficacy of osimertinib for the treatment of EGFR T790M mutation positive non-small-cell lung cancer. Expert Rev Anticancer Ther. 2016; 16:383-90.
7. Takeda M, Nakagawa K. First- and second-generation EGFR-TKIs are all replaced to osimertinib in chemonaïve EGFR mutation-positive non-small cell lung cancer. International Journal of Molecular Sciences. 2019; 20:146. doi: 10.3390/ijms20010146.
8. Goss G, Tsai C-M, Shepherd F A, Bazhenova L, Lee J S, Chang G-C, et al. Osimertinib for pretreated EGFR Thr790Met-positive advanced non-small-cell lung cancer (AURA2): a multicentre, open-label, single-arm, phase 2 study. Lancet Oncol. 2016; 17:1643-52. doi: 10.1016/S1470-2045 (16) 30508-3.
9. Kari C, Chan T O, Rocha de Quadros M, Rodeck U. Targeting the epidermal growth factor receptor in cancer: Apoptosis takes center stage. Cancer Res. 2003; 63:1-5.
10. Mascia F, Mariani V, Girolomoni G, Pastore S. Blockade of the EGF Receptor Induces a Deranged Chemokine Expression in Keratinocytes Leading to Enhanced Skin Inflammation. 2003.
11. Cubero D I G, Abdalla B M Z, Schoueri J, Lopes F I, Turke K C, Guzman J, et al. Cutaneous side effects of molecularly targeted therapies for the treatment of solid tumors. Drugs Context. 2018; 7:1-11.
12. Peréz-Soler R, Saltz L. Cutaneous adverse effects with HER1/EGFR-targeted agents: is there a silver lining? J Clin Oncol. 2005; 23:5235-46. doi: 10.1200/JCO.2005.00.6916.
13. Yerushalmi R, Woods R, Ravdin P M, Hayes M M, Gelmon K A. Ki67 in breast cancer: prognostic and predictive potential. Lancet Oncol. 2010; 11:174-83. doi: 10.1016/S1470-2045 (09) 70262-1.
14. Sandilands A, Sutherland C, Irvine A D, McLean W H I. Filaggrin in the frontline: role in skin barrier function and disease. J Cell Sci. 2009; 122 Pt 9:1285-94. doi: 10.1242/jcs.033969.
15. Getsios S, Amargo E V., Dusek R L, Ishii K, Sheu L, Godsel L M, et al. Coordinated expression of desmoglein 1 and desmocollin 1 regulates intercellular adhesion. Differentiation. 2004; 72:419-33. doi: 10.1111/j.1432-0436.2004.07208008.x.
16. Steinert P M, Marekov L N. Direct evidence that involucrin is a major early isopeptide cross-linked component of the keratinocyte cornified cell envelope. J Biol Chem. 1997; 272:2021-30. doi: 10.1074/jbc.272.3.2021.
17. Paul T, Schumann C, Rüdiger S, Boeck S, Heinemann V, Kächele V, et al. Cytokine regulation by epidermal growth factor receptor inhibitors and epidermal growth factor receptor inhibitor associated skin toxicity in cancer patients. Eur J Cancer. 2014; 50:1855-63.
18. Danilenko D M, Phillips G D L, Diaz D. In Vitro Skin Models and Their Predictability in Defining Normal and Disease Biology, Pharmacology, and Toxicity. Toxicol Pathol. 2016; 44:555-63. doi: 10.1177/0192623316632074.
19. Klaeger S, Heinzlmeir S, Wilhelm M, Polzer H, Vick B, Koenig P-A, et al. The target landscape of clinical kinase drugs. Science. 2017; 358. doi: 10.1126/science.aan4368.
20. Nicholson D W, Ali A, Thornberry N A, Vaillancourt J P, Ding C K, Gallant M, et al. Identification and inhibition of the ICE/CED-3 protease necessary for mammalian apoptosis. Nature. 1995; 376:37-43. doi: 10.1038/376037a0.
21. Rosell R, Carcereny E, Gervais R, Vergnenegre A, Massuti B, Felip E, et al. Erlotinib versus standard chemotherapy as first-line treatment for European patients with advanced EGFR mutation-positive non-small-cell lung cancer (EURTAC): A multicentre, open-label, randomised phase 3 trial. Lancet Oncol. 2012; 13:239-46. doi: 10.1016/S1470-2045 (11) 70393-X.
22. Yang Y, Zhang Y, Cao Z, Ji H, Yang X, Iwamoto H, et al. Anti-VEGF- and anti-VEGF receptor-induced vascular alteration in mouse healthy tissues. Proc Natl Acad Sci USA. 2013; 110:12018-23. doi: 10.1073/pnas.1301331110.
23. Cross D A E E, Ashton S E, Ghiorghiu S, Eberlein C, Nebhan C A, Spitzler P J, et al. AZD9291, an irreversible EGFR TKI, overcomes T790M-mediated resistance to EGFR inhibitors in lung cancer. Cancer Discov. 2014; 4:1046-61. doi: 10.1158/2159-8290.CD-14-0337.
24. Chu C, Choi J, Eaby-Sandy B, Langer C J, Lacouture M E. Osimertinib: A Novel Dermatologic Adverse Event Profile in Patients with Lung Cancer. Oncologist. 2018; 23:891-9.
25. Li J, Brahmer J, Messersmith W, Hidalgo M, Baker S D. Binding of gefitinib, an inhibitor of epidermal growth factor receptor-tyrosine kinase, to plasma proteins and blood cells: In vitro and in cancer patients. Invest New Drugs. 2006; 24:291-7.
26. Swaisland H C, Smith R P, Laight A, Kerr D J, Ranson M, Wilder-Smith C H, et al. Single-dose clinical pharmacokinetic studies of gefitinib. Clin Pharmacokinet. 2005; 44:1165-77.
27. Togashi Y, Masago K, Fukudo M, Terada T, Ikemi Y, Kim Y H, et al. Pharmacokinetics of erlotinib and its active metabolite OSI-420 in patients with non-small cell lung cancer and chronic renal failure who are undergoing hemodialysis. J Thorac Oncol. 2010; 5:601-5. doi: 10.1097/JTO.0b013e3181d32287.

28. Herbst R S, Johnson D H, Mininberg E, Carbone D P, Henderson T, Kim E S, et al. Phase I/II trial evaluating the anti-vascular endothelial growth factor monoclonal antibody bevacizumab in combination with the HER-1/epidermal growth factor receptor tyrosine kinase inhibitor erlotinib for patients with recurrent non-small-cell lung cancer. J Clin Oncol. 2005; 23:2544-55.
29. Wind S, Schnell D, Ebner T, Freiwald M, Stopfer P. Clinical Pharmacokinetics and Pharmacodynamics of Afatinib. Clin Pharmacokinet. 2017; 56:235-50. doi: 10.1007/s40262-016-0440-1.
30. EMEA. European Medicines Agency: EMEA/H/C/002280-Annual report of the European Medicines Agency 2013. 2013; 44 July. http://www.ema.europa.eu/docs/en_GB/document_library/EPAR_-_Public_assessment_report/human/002280/WC500152394.pdf.
31. Wind S, Schmid M, Erhardt J, Goeldner R G, Stopfer P. Pharmacokinetics of afatinib, a selective irreversible ErbB family blocker, in patients with advanced solid tumours. Clin Pharmacokinet. 2013; 52:1101-9.
32. Hudachek S F, Gustafson D L. Physiologically based pharmacokinetic model of lapatinib developed in mice and scaled to humans. J Pharmacokinet Pharmacodyn. 2013; 40:157-76. doi: 10.1007/s10928-012-9295-8.
33. Burris H A, Hurwitz H I, Dees E C, Dowlati A, Blackwell K L, O'Neil B, et al. Phase I safety, pharmacokinetics, and clinical activity study of lapatinib (GW572016), a reversible dual inhibitor of epidermal growth factor receptor tyrosine kinases, in heavily pretreated patients with metastatic carcinomas. J Clin Oncol. 2005; 23:5305-13. doi: 10.1200/JCO.2005.16.584.
34. Giri N, Masters J C, Plotka A, Liang Y, Boutros T, Pardo P, et al. Investigation of the impact of hepatic impairment on the pharmacokinetics of dacomitinib. Invest New Drugs. 2015; 33:931-41.
35. Reckamp K L, Giaccone G, Camidge D R, Gadgeel S M, Khuri F R, Engelman J A, et al. A phase 2 trial of dacomitinib (PF-00299804), an oral, irreversible pan-HER (human epidermal growth factor receptor) inhibitor, in patients with advanced non-small cell lung cancer after failure of prior chemotherapy and erlotinib. Cancer. 2014; 120:1145-54.
36. Reddy V P, Walker M, Sharma P, Ballard P, Vishwanathan K. Development, verification, and prediction of osimertinib drug-drug interactions using PBPK modeling approach to inform drug label. CPT Pharmacometrics Syst Pharmacol. 2018; 7:321-30.
37. Rais R, Zhao M, He P, Xu L, Deeken J F, Rudek M A. Quantitation of unbound sunitinib and its metabolite N-desethyl sunitinib (SU12662) in human plasma by equilibrium dialysis and liquid chromatography-tandem mass spectrometry (LC/MS/MS): application to a pharmacokinetic study. Biomed Chromatogr. 2012; 26:230-3.
38. Fabian M A, Biggs W H, Treiber D K, Atteridge C E, Azimioara M D, Benedetti M G, et al. A small molecule-kinase interaction map for clinical kinase inhibitors. Nat Biotechnol. 2005; 23:329-36. doi: 10.1038/nbt1068.
39. Villarroel M C, Pratz K W, Xu L, Wright J J, Smith B D, Rudek1 M A. Plasma protein binding of sorafenib, a multi kinase inhibitor: in vitro and in cancer patients. Invest New Drugs. 2012; 30:1-15.
40. Davis M I, Hunt J P, Herrgard S, Ciceri P, Wodicka L M, Pallares G, et al. Comprehensive analysis of kinase inhibitor selectivity. Nat Biotechnol. 2011; 29:1046-51. doi: 10.1038/nbt.1990.
41. U.S. Pat. No. 10,092,495
42. U.S. Pat. No. 10,175,230
43. U.S. Published Application No. 20190242880

SUPPLEMENTARY DATA

| | | | DSG | | | | | |
|---|---|---|---|---|---|---|---|---|
| | #Run | Dose/response | 3 nM | 10 nM | 30 nM | 100 nM | 1 μM | 10 μM |
| Enzalutamide | 1st Run | No | NA | NA | NA | −6% | −6% | −12% |
| Nevirapine | 1st Run | Yes (DSG) | NA | NA | NA | −8% | −15% | −28% |
| Acalabrutinib | 1st Run | Yes (DSG, IVL, FLG) | NA | NA | NA | −26% | −15% | −7.50% |
| Vandetanib | 1st Run | Yes (DSG, IVL, FLG) | NA | NA | NA | 5% | 30% | Tox |
| Vemurafenib | 1st Run | Yes (DSG, IVL, FLG) | NA | NA | NA | −26% | −33% | −58% |
| Gefitinib | 2nd Run | Yes (DSG) | −8% | 0% | 15% | 41% | NA | NA |
| Erlotinib | 2nd Run | No | −7% | −2% | 1% | 36% | NA | NA |
| Dacomitinib | 2nd Run | Yes (DSG, IVL, FLG) | 10.00% | 32% | 54% | Tox | NA | NA |
| Lapatinib | 2nd Run | Yes (DSG, IVL, FLG) | −6.20% | 9.6% | 29% | 47% | NA | NA |
| Afatinib | 2nd Run | Yes (DSG, IVL, FLG) | 38% | 67% | 87% | NA | NA | NA |
| Sorafenib | 1st Run | No | NA | NA | NA | −32% | 8% | Tox |
| | 2nd Run | No | NA | −8% | NA | −9% | 41% | NA |
| Sunitinib | 1st Run | Yes (FLG) | NA | NA | NA | −10% | −11% | 27% |
| | 2nd Run | No | NA | 15% | NA | −16% | −4% | NA |
| Acetaminophen | 1st Run | No | NA | NA | NA | −14% | −10% | −19% |
| | 2nd Run | No | NA | NA | NA | 18% | 16% | 4% |
| Osimertinib | 1st Run | No | NA | NA | NA | 18% | Tox | Tox |
| | 2nd Run | No | −3% | −7% | 7% | NA | NA | NA |

| IVL | | | | | | |
|---|---|---|---|---|---|---|
| | 3 nM | 10 nM | 30 nM | 100 nM | 1 μM | 10 μM |
| Enzalutamide | NA | NA | NA | 9.30% | 6.20% | 2% |
| Nevirapine | NA | NA | NA | 17% | 15% | 20% |
| Acalabrutinib | NA | NA | NA | 11% | 15% | 25% |
| Vandetanib | NA | NA | NA | 25% | 51% | Tox |
| Vemurafenib | NA | NA | NA | -11% | -24% | -40% |
| Gefitinib | 23% | 8% | 23% | 29% | NA | NA |
| Erlotinib | 13% | 16% | 22% | 35% | NA | NA |
| Dacomitinib | 15% | 31% | 60% | Tox | NA | NA |
| Lapatinib | 17% | 14% | 30% | 48% | NA | NA |
| Afatinib | NA | NA | 12% | 16% | 27% | NA |
| Sorafenib | NA | NA | NA | 0% | -6% | Tox |
| | NA | 6% | NA | 2% | 5% | NA |
| Sunitinib | NA | NA | NA | 14% | 9% | 24% |
| | NA | 0% | NA | 0% | -1% | NA |
| Aceta-minophen | NA | NA | NA | 10% | 7% | 10% |
| | NA | NA | NA | 4% | -2% | 8% |
| Osimertinib | NA | NA | NA | 20% | Tox | Tox |
| | 6% | 8% | 7% | NA | NA | NA |

| FLG | | | | | | |
|---|---|---|---|---|---|---|
| | 3 nM | 10 nM | 30 nM | 100 nM | 1 μM | 10 μM |
| Enzalutamide | NA | NA | NA | 2% | 9.80% | -1% |
| Nevirapine | NA | NA | NA | 7% | 8% | 2% |
| Acalabrutinib | NA | NA | NA | 6% | 15% | 33% |
| Vandetanib | NA | NA | NA | 14.50% | 42% | Tox |
| Vemurafenib | NA | NA | NA | 23% | 65% | 126% |
| Gefitinib | 10% | 3% | 5% | 28% | NA | NA |
| Erlotinib | 6% | 0% | 10% | 34% | NA | NA |
| Dacomitinib | 8% | 25% | 31% | Tox | NA | NA |
| Lapatinib | 7% | 9% | 20% | 18% | NA | NA |
| Afatinib | 4% | 12% | 19% | NA | NA | NA |
| Sorafenib | NA | NA | NA | -7% | -24% | Tox |
| | NA | -22% | NA | -28% | -22% | NA |
| Sunitinib | NA | NA | NA | 5% | 22% | 101% |
| | NA | -5% | NA | -12% | 7.50% | NA |
| Acetaminophen | NA | NA | NA | 2% | 0% | 1% |
| | NA | NA | NA | -5% | -4.0% | -12% |
| Osimertinib | NA | NA | NA | 16% | Tox | Tox |
| | -12% | -6% | 2% | NA | NA | NA |

| Gefitinib | | |
|---|---|---|
| Cmax | Kd (nM) | Unbound fraction |
| [25] | [19] | [26] |

MoA:

| Erlotinib | | |
|---|---|---|
| Cmax | Kd (nM) | Unbound fraction |
| [27] | [19] | [27] |

MoA: [28]

| Afatinib | | |
|---|---|---|
| Cmax | Kd (nM) | Unbound fraction |
| [29] | [19] | [30] |

MoA: [31]

| Lapatinib | | |
|---|---|---|
| Cmax | Kd (nM) | Unbound fraction |
| [32] | [19] | [32] |

MoA: [33]

| Dacomitinib | | |
|---|---|---|
| Cmax | Kd (nM) | Unbound fraction |
| [34] 30 mg/day | [19] | [34] |

MoA: [35]

| Osimertinib | | |
|---|---|---|
| Cmax | Kd (nM) | Unbound fraction |
| [36] | [19] | [36] |

MoA: [23]

| Sunitinib | | |
|---|---|---|
| Cmax | Kd (nM) | Unbound fraction |
| [37] | [38] | [37] |

| Sorafenib | | |
|---|---|---|
| Cmax | Kd (nM) | Unbound fraction |
| [39] | [40] | [39] |

The invention claimed is:

1. An in vitro or ex vivo epidermal tridimensional model comprising:
- a first reconstructed human epidermis, the first reconstructed human epidermis representing a first stage of maturity;
- a second reconstructed human epidermis, the second reconstructed human epidermis representing a second stage of maturity different than the first stage of maturity;
- calcium;
- an air liquid interface;
- a cancer therapeutic that stimulates chronic drug exposure; and
- a means to measure trans-epidermal water loss rate at each of the first reconstructed human epidermis and the second reconstructed human epidermis,
- wherein the model functionally reproduces barrier compromise due to the chronic drug exposure to the cancer therapeutic.

2. A method to test a cancer therapeutic to determine if the cancer therapeutic produces skin related side effects, comprising comparing the measured trans-epidermal water loss rate of the cancer therapeutic in claim 1 to a control; wherein an increase in trans-epidermal water loss rate of the cancer therapeutic as compared to the control indicates skin barrier impairment.

3. A method to test a composition to determine if the composition can prevent the effect the cancer therapeutic has on skin barrier structure and function, measuring the trans-epidermal water loss rate in the model of claim 1; introducing the composition to said model of claim 1; measuring trans-epidermal water loss rate with the composition present; comparing trans-epidermal water loss rate with the composition present to trans-epidermal water loss without the composition present; wherein a decrease in trans-epidermal water loss rate indicates that the composition can prevent the effect the cancer therapeutic has on skin barrier structure and function.

4. The method of claim 1, wherein the measured trans-epidermal water loss rate is measured using Tewitro® TW 24, at 33° C.

5. The method of claim 4, wherein measurements to measure the trans-epidermal water loss rate are taken after 1 hour stabilization.

6. The method of claim 1, wherein the cancer therapeutic is selected from the group consisting of Sunitinib; Sorafenib; Gefitinib; Erlotinib; Afatinib; Lapatinib; Dacomitinib; Osimertinib; and Osimertinib.

7. The method of claim 1, wherein the cancer therapeutic is afatinib.

* * * * *